United States Patent
Adler et al.

(10) Patent No.: US 6,832,843 B2
(45) Date of Patent: Dec. 21, 2004

(54) ILLUMINATION FOR INSPECTING SURFACES OF ARTICLES

(75) Inventors: Avraham Adler, Nof Ayalon (IL); Moshe Ben Shlomo, Macabbim (IL)

(73) Assignee: Orbotech, Ltd., Yavne (IL)

( * ) Notice: Subject to any disclaimer, the term of this patent is extended or adjusted under 35 U.S.C. 154(b) by 0 days.

(21) Appl. No.: 10/200,147

(22) Filed: Jul. 23, 2002

(65) Prior Publication Data

US 2002/0181233 A1 Dec. 5, 2002

Related U.S. Application Data

(62) Division of application No. 09/565,500, filed on May 5, 2000, now Pat. No. 6,437,312.

(30) Foreign Application Priority Data

Aug. 5, 1999 (IL) ................................. 131284

(51) Int. Cl.[7] ................................. F21V 7/08
(52) U.S. Cl. ..................... 362/247; 362/297; 362/346; 362/554
(58) Field of Search ................. 355/70; 358/473–475, 358/480–482, 484; 362/241, 245, 247, 259, 268, 297, 346, 554

(56) References Cited

U.S. PATENT DOCUMENTS

| | | | |
|---|---|---|---|
| 804,996 A | | 11/1905 | Anthony ..................... 359/365 |
| 1,278,026 A | * | 9/1918 | Salto ........................... 362/241 |
| 1,687,069 A | * | 10/1928 | Iser .............................. 355/70 |

(List continued on next page.)

FOREIGN PATENT DOCUMENTS

| EP | 0 526 070 A2 | 2/1993 |
|---|---|---|
| GB | 2 142 444 A | 1/1985 |
| JP | 55163942 A * | 12/1980 ................. 358/484 |
| JP | 57-19712 | 2/1982 |
| JP | 59-123980 | 7/1984 |
| JP | 62103548 | 5/1987 |
| JP | 1105852 | 7/1989 |
| WO | WO 99/66314 | 12/1999 |

OTHER PUBLICATIONS

LaMuth, Henry L., Applied Optics, "Measurements on Lambertian objects: some novel approaches," vol. 14, No. 5, May 1975, pp. 1150–1155.

Vortek Industries Ltd., advertisement, "High Irradiance Reflectors," 2 pages, Dec. 12, 1990.

Snail, Keith A., "Reflectometer Design Using Nonimaging Optics," 19 pages, (undated but prior to the filing date of this application).

Bradenberg, W. M., Journal of the Optical Society of America, "Focusing Properties of Hemispherical and Ellipsoidal Mirror Reflectometers," vol. 54, No. 10, pp. 1235–1237, Oct. 1964.

Jacquez, John A., et al., Journal of the Optical Society of America, "An Integrating Sphere for Measuring Diffuse Reflectance in the Near Infrared," vol. 45, No. 10, pp. 781–785, Oct. 1955.

Gindele, K., et al., Applied Optics, "Spectral reflectance measurements using an integrating sphere in the infrared,", vol. 24, No. 12, pp. 1757–1760, Jun. 15, 1985.

(List continued on next page.)

Primary Examiner—Alan Cariaso
(74) Attorney, Agent, or Firm—Banner & Witcoff, Ltd.

(57) ABSTRACT

An illumination system including at least one reflector subtending an angle with respect to a location on a surface of an article, and first and second light sources, the first and second light sources each providing a light output, the light outputs from both of the first and second light sources being directed to impinge on the location on the surface of an article within the angle, at least one of the light outputs being reflected by the reflector.

12 Claims, 6 Drawing Sheets

U.S. PATENT DOCUMENTS

| | | | |
|---|---|---|---|
| 2,257,881 A | 10/1941 | Jaros | 362/235 |
| 2,352,693 A | 7/1944 | Davidson | 105/198.2 |
| 3,164,781 A * | 1/1965 | Goldberg | 362/247 |
| 3,229,564 A | 1/1966 | Meltzer | 356/446 |
| 3,251,984 A | 5/1966 | Colterjohn | 362/11 |
| 3,270,194 A | 8/1966 | Lee | 362/218 |
| 3,277,773 A | 10/1966 | White | 356/323 |
| 3,365,720 A | 1/1968 | Kelleher | 343/837 |
| 3,375,361 A | 3/1968 | Thompson et al. | 362/6 |
| 3,375,752 A | 4/1968 | Fairbanks et al. | 355/70 |
| 3,428,397 A | 2/1969 | Elmer | 399/221 |
| 3,498,714 A | 3/1970 | Elmer | 355/70 |
| 3,560,729 A | 2/1971 | Liberman | 362/294 |
| 3,620,621 A * | 11/1971 | Rachwal et al. | 355/70 |
| 3,663,083 A | 5/1972 | Friedman et al. | 385/146 |
| 3,763,348 A | 10/1973 | Costello | 392/423 |
| 3,806,256 A | 4/1974 | Ishak | 356/446 |
| 3,825,322 A | 7/1974 | Mast | 359/799 |
| 3,920,311 A | 11/1975 | Tsuda et al. | 359/387 |
| 3,923,381 A | 12/1975 | Winston | 359/852 |
| 3,949,214 A * | 4/1976 | Jones et al. | 362/247 |
| 3,957,031 A | 5/1976 | Winston | 126/695 |
| 4,002,499 A | 1/1977 | Winston | 136/206 |
| 4,003,638 A | 1/1977 | Winston | 359/852 |
| 4,006,355 A | 2/1977 | Shemitz et al. | 362/217 |
| 4,008,946 A | 2/1977 | Tsuda et al. | 359/372 |
| 4,027,151 A | 5/1977 | Barthel | 362/217 |
| 4,045,246 A | 8/1977 | Mlavsky et al. | 136/246 |
| 4,095,905 A | 6/1978 | Kuni et al. | 356/430 |
| 4,220,982 A | 9/1980 | Martino | 362/97 |
| 4,223,346 A | 9/1980 | Neiheisel et al. | 348/131 |
| 4,255,055 A | 3/1981 | Schave | 356/613 |
| 4,287,554 A | 9/1981 | Wolff | 362/218 |
| 4,319,847 A | 3/1982 | Howarth | 356/431 |
| 4,320,442 A | 3/1982 | McCamy | 362/301 |
| 4,321,630 A * | 3/1982 | Kramer | 358/480 |
| 4,360,275 A | 11/1982 | Louderback | 356/446 |
| 4,421,410 A | 12/1983 | Karasaki | 356/394 |
| 4,423,470 A | 12/1983 | Naito et al. | 362/17 |
| 4,441,817 A | 4/1984 | Pryor | 356/615 |
| 4,449,818 A | 5/1984 | Yamaguchi et al. | 356/237.3 |
| 4,460,942 A | 7/1984 | Pizzuti et al. | 362/217 |
| 4,464,050 A | 8/1984 | Kato et al. | 356/239.1 |
| 4,498,742 A | 2/1985 | Uehara | 359/385 |
| 4,500,202 A | 2/1985 | Smyth | 382/100 |
| 4,506,152 A | 3/1985 | Gupta | 250/216 |
| 4,531,180 A | 7/1985 | Hernandez | 362/297 |
| 4,555,727 A | 11/1985 | Nun et al. | 348/131 |
| 4,595,947 A * | 6/1986 | Brueggemann | 358/481 |
| 4,597,665 A | 7/1986 | Galbraith et al. | 356/239.8 |
| 4,661,706 A | 4/1987 | Messerschmidt et al. | 250/341.8 |
| 4,671,663 A | 6/1987 | Sick | 356/430 |
| 4,688,907 A | 8/1987 | Kleinberg | 359/377 |
| 4,692,690 A | 9/1987 | Hara et al. | 356/394 |
| 4,693,601 A | 9/1987 | Dabelstein et al. | 356/237.2 |
| 4,710,638 A | 12/1987 | Wood | 250/492.1 |
| 4,714,527 A | 12/1987 | Hofmeier et al. | 205/789 |
| 4,718,767 A | 1/1988 | Hazama | 356/389 |
| 4,730,895 A | 3/1988 | Siedband et al. | 385/121 |
| 4,758,888 A | 7/1988 | Lapidot | 348/91 |
| 4,795,911 A | 1/1989 | Kohno et al. | 250/559.1 |
| 4,801,810 A | 1/1989 | Koso | 250/559.3 |
| 4,815,858 A | 3/1989 | Snail | 356/446 |
| 4,816,686 A | 3/1989 | Hara et al. | 250/458.1 |
| 4,821,114 A | 4/1989 | Gebhardt | 358/512 |
| 4,824,194 A | 4/1989 | Karasawa | 385/146 |
| 4,859,064 A | 8/1989 | Messerschmidt et al. | 356/446 |
| 4,877,326 A | 10/1989 | Chadwick et al. | 356/394 |
| 4,881,802 A | 11/1989 | Stankewitz | 359/387 |
| 4,900,153 A | 2/1990 | Weber et al. | 356/430 |
| 4,922,107 A | 5/1990 | Rabl et al. | 250/504 R |
| 4,933,817 A | 6/1990 | Mochizuki et al. | 362/33 |
| 4,938,555 A | 7/1990 | Savage | 385/18 |
| 5,058,928 A | 10/1991 | Watson | 285/38 |
| 5,085,517 A | 2/1992 | Chadwick et al. | 356/394 |
| 5,153,668 A | 10/1992 | Katzir et al. | 356/237.2 |
| 5,288,987 A | 2/1994 | Vry et al. | 250/201.3 |
| 5,357,335 A | 10/1994 | Sparks et al. | 356/237.2 |
| 5,483,603 A | 1/1996 | Luke et al. | 382/147 |
| 5,524,152 A | 6/1996 | Bishop et al. | 382/165 |
| 5,586,058 A | 12/1996 | Aloni et al. | 702/35 |
| 5,619,429 A | 4/1997 | Aloni et al. | 700/279 |
| 5,673,122 A * | 9/1997 | Omori | 358/484 |
| 5,760,950 A | 6/1998 | Maly et al. | 359/368 |
| 5,774,573 A | 6/1998 | Caspi et al. | 382/141 |
| 6,043,932 A | 3/2000 | Kusunose | 359/368 |
| 6,168,296 B1 * | 1/2001 | Yoneda | 362/268 |

OTHER PUBLICATIONS

Edwards, D. K., et al., Applied Optics, "*Integrating Sphere for Imperfectly Diffuse Samples,*", vol. 51, pp. 1279–1288, Nov., 1961.

Goodman, Douglas S., Applied Optics, "*Illuminator for dark field microscopy,*" vol. 23, No. 16, pp. 2670–2671, Aug. 15, 1984.

Goodman, Douglas S., Applied Optics, "*Illuminators based on fiber rings,*" vol. 24, No. 11, pp. 1560–1562, Jun. 1, 1985.

* cited by examiner

ILLUMINATION FOR INSPECTING SURFACES OF ARTICLES

RELATED APPLICATION

The present application is a division of U.S. patent application Ser. No. 09/565,500, filed May 5, 2000, U.S. Pat. No. 6,437,312.

FIELD OF THE INVENTION

The present invention relates to visual inspection of surfaces of articles, and more particularly to an illuminator for the automated optical inspection of ball grid array substrates, lead frames and printed circuit boards.

BACKGROUND OF THE INVENTION

Apparatus and methods useful for illuminating substantially flat patterned surfaces of articles, such as electrical circuits on printed circuit boards (PCBs), ball grid array substrates (BGAs) reticles, semiconductors and other similar articles, during the automated optical inspection thereof are well known in the art.

During automatic optical inspection of flat patterned surfaces of articles, such as electrical circuits on PCBs and BGAs, the surface is illuminated by intense broad spectrum illumination while the article is transported beneath a sensor, such as a CCD or TDI camera. Conventionally, the sensors acquire scanned gray level images of the surface. Various materials which appear on the surface of an article each have different reflective properties and reflect illumination at a different level of intensity. For example, copper which defines conductors, various metal platings on the conductors, and the substrate itself each have different reflective properties. The reflected intensities in the image are sensed and automatically processed and analyzed to determine the presence of defects in the patterns on the surfaces.

The surfaces of electrical circuits being inspected, although substantially flat, generally exhibit a topographical relief that results both from the cross-sectional configuration of conductors as well as the surface microstructure thereof. Typically, very intense illumination impinging on a surface of an article being inspected over a solid angle of incidence is employed to mitigate negative affects of the topographical relief The following patents are believed to represent the state of the art in high intensity illumination for the inspection of substantially flat patterned article surfaces such as electrical circuits on printed circuit boards (PCBs), ball grid array substrates (BGAs), lead frames, reticles and semiconductors:

U.S. Pat. No. 4,421,410 to Karasaki describes an illuminator comprising a half reflecting mirror disposed above a printed wiring board. Concentrated light is reflected off the mirror and directed onto the wiring board at an angle substantially normal to the surface of the board and diffuse light emanating from fiber optics is simultaneously directed onto the surface at a large angle of incidence. An image of a line on the surface is transmitted through the mirror to a sensor.

U.S. Pat. No. 4,877,326 to Chadwick describes a high intensity illuminator providing focused quasi lambertian illumination to a region of the surface of an article to be inspected. The illuminator includes a half reflecting mirror, first and second and third elliptical cylindrical reflectors and first, second and third lamps, all having mutually parallel elongate axes. Two of the reflectors and two of the light sources are spaced from each other and illuminate the surface with focused light at a large angle of incidence. The half reflecting mirror, the third reflector, and the third lamp are arranged to reflect focused light along an axis normal to the surface to fill the gap between the first and second reflectors. Each lamp is located at one focus of a reflector, and the illuminated region is located at the second focus of the reflectors. Forth and fifth planar reflectors are provided at the longitudinal ends of the first, second and third reflectors, and a sensor is provided to image the illuminated region by sensing light reflected therefrom which passes through the half reflecting mirror.

Israel patent 81450 in the name of Orbotech Ltd. describes a high intensity illuminator similar in structure to that described in U.S. Pat. No. 4,877,326, but employing light supplied via fiber optics, and effectively having a numerical aperture substantially smaller than the numerical aperture of the apparatus described in U.S. Pat. No. 4,877,326.

U.S. Pat. No. 5,058,982 to Katzir describes a high intensity illuminator comprising a beam splitter cube and first, second and third elliptical cylindrical reflectors, two of which are spaced from each other. Light received via fiber optics is provided at one focus of each reflector. The reflectors are oriented so that the second focus of each reflector illuminates a region of a surface to be inspected. A third illuminator and a condensing lens are provided and oriented to direct light through the beam splitter and onto the surface to be inspected along an axis normal thereto. A sensor is oriented to receive light reflected from the surface via the beam splitter cube.

U.S. Pat. No. 5,153,668 to Katzir describes an illuminator for illuminating an area to be inspected on the surface of an article, in which the illumination is configured to be substantially circularly symmetric over a solid angle around an optical axis normal to the surface. A sensor is provided to image the surface through a gap between the illuminators.

U.S. Pat. No. 4,801,810 to Koso describes an elliptical reflector, comprising approximately one half of an elliptical cylinder, which is used to illuminate the surface of a printed circuit board. The axis of the elliptical cylinder is oblique to the surface of the printed circuit board. A lamp is disposed under the reflector at one focus of the ellipse, while the region illuminated is located at the other focus. An imaging system images the illuminated region through an aperture formed in the reflector.

The illuminator employed in Inspire™ automated optical systems manufactured and sold by Orbotech Ltd., and described in copending PCT application WO 9966314 is a high intensity illuminator comprising a first light source that emits light over a continuous wide angle of illumination toward a surface of an article to be inspected and has a blocking element that blocks a portion of the continuous angle of illumination to form two separate portions of illumination. A second light source is employed to supply illumination to the region blocked by the blocking element. Concentrating optics are provided to concentrate the illumination onto the article. The illumination is provided at a first angle to the normal, and an imaging sensor is provided to image the illuminated region of the article at a second angle to the normal.

Systems which image a surface to be inspected along an imaging axis that is normal to the surface being inspected typically employ at least three separate sources of illumination. In systems that employ less than three sources of illumination to provide an intense solid angle of illumination, the surface is imaged along an axis which is oriented at a non-normal angle thereto.

Additionally, conventional systems that illuminate and image a surface to be inspected along an axis that is normal to the surface being illuminated acquire images via beam splitting apparatus that introduces undesired aberrations into the image.

SUMMARY OF THE INVENTION

The present invention generally seeks to provide high intensity illumination for the automated optical inspection of patterned articles in which two light sources together provide a solid angle of illumination, the spatial uniformity of which is adjustable.

One aspect of a preferred embodiment of the invention provides illumination of a region on the surface of an article over a solid angle using two independently adjustable sources of illumination, wherein the axis of at least one source of illumination is substantially normal to the surface. Preferably, the region illuminated is imaged by a sensor whose axis of imaging is also substantially normal to the surface.

According to another aspect of a preferred embodiment of the invention, a region of an article to be inspected is illuminated with a first illuminator, including a reflective surface which is apertured at a location which overlies the region to be inspected. Supplemental illumination of the region is provided through the aperture and a sensor images the region to be inspected by sensing light reflected therefrom through the aperture.

According to still another aspect of a preferred embodiment of the invention, an imaging system is provided in which the surface of the article is illuminated by a solid angle of illumination to illuminate a line, and wherein a sensor is provided to image the illuminated region in a manner that avoids transmitting reflected light from the region through a beam splitter or through a partially reflected mirror en route to the sensor.

Preferably, a partially reflective planar mirror is oriented along an imaging axis normal to the surface. Illumination is transmitted through the partially reflective planar mirror to provide illumination along an axis normal to the surface. Light reflected from the surface is reflected by the partially reflective mirror into the sensor for imaging the surface.

In accordance with still another aspect of a preferred embodiment of the invention, an illuminator is provided to illuminate a linear region along a surface of an article during automated optical inspection thereof. The illuminator is configured to provide a broad angle of illumination from a multiplicity of illumination sources. At least one illumination source provides illumination along an axis which is substantially normal to the surface. Illumination from that source is passed through an optical element that introduces astigmatism into the illumination along an axis of astigmatism that is substantially colinear to the linear region, thereby smearing the illumination along the illuminated linear region.

Another aspect of a preferred embodiment of the invention provides an illuminator for illuminating a linear region along a surface of a substrate with a broad angle of illumination. The illumination is provided by a plurality of sources, wherein a first source of illumination provides illumination along an axis that is substantially normal to the surface of an article. The illumination provided by the first source is passed through an optical assembly configured to introduce astigmatism into the illumination provided by the first source. The astigmatism is oriented along an axis that is substantially colinear to the linear region being illuminated. Preferably, an imaging sensor is provided to image the linear illuminated region at least partially along an axis that is normal to the surface of the article.

According to still another aspect of the invention, there is provided a substantially telecentric imaging system for imaging a region of a surface of an object during automated optical inspection thereof. The system comprises a plurality of lenses and sensors operative simultaneously to acquire a plurality of images of mutually overlapping regions. Preferably, the maximum angle at which any pixel is imaged is less than approximately 5° and preferably less than 3.7° to the normal with respect to the surface. The imaging path of at least one of the sensors is preferably folded by a folding mirror which is located in a region adjacent to a waist in the imaging paths of the other sensors.

According to another aspect of the invention, there is provided an inspection system for automatically inspecting patterned articles. Illumination in a first spectral range is provided on one surface of the article and illumination in a second spectral range, distinguishable from the first range, is provided on the opposite surface of the article. Sensors are employed to sense the intensity of reflected light in the first spectral range, and to sense the intensity of transmitted light in the second spectral range. Patterns on the surface of the article are inspected based on reflected light intensity in the first spectral range. The presence and pattern of desired and undesired apertures in the article are inspected based on transmitted light in the second spectral range.

There is thus provided in accordance with a preferred embodiment of the present invention an illumination system including at least one reflector subtending an angle with respect to a location on a surface of an article, and first and second light sources, the first and second light sources each providing a light output, the light outputs from both of the first and second light sources being directed to impinge on the location on the surface of an article within the angle, at least one of the light outputs being reflected by the reflector.

Further in accordance with a preferred embodiment of the present invention the reflector is formed with a light transmissive region to permit a light output from a first one of a the first and second light sources to pass therethrough. Preferably the light transmissive region is an aperture formed in the reflector. Preferably the illumination system also includes an optical element disposed intermediate the first one of the first and second light sources and the aperture for directing the light output of the first one of the first and second light sources through the aperture. Additionally the optical element also includes at least one reflecting surface.

Alternatively the illumination system may also include an optical assembly disposed along an optical path extending between the optical element and the location on the surface of an article for directly light reflected from the location on the surface of an article to a light sensor. Preferably the optical assembly is generally transmissive to the light output of the first one of the first and second light sources directed through the aperture onto the location on the surface of an article and generally reflective of light reflected from the location on the surface of an article.

Furthermore the illumination system may also include a reflective surface disposed intermediate a second one of the first and second light sources and the reflector for directing the light output of the second one of the first and second light sources onto the reflector.

Additionally in accordance with a preferred embodiment of the present invention the at least one reflector is an elliptical reflector and the second one of the first and second light sources and the location on the surface of an article are each located at or near a locus of the elliptical reflector. Preferably the at least one reflector includes two spaced apart reflectors which together define a section of an ellipse. The spaced apart reflectors are preferably separated by an aperture.

Alternatively the first and second light sources may also be independently controllable light sources.

There is also provided in accordance with a preferred embodiment of the present invention an illumination system including a cylindrical reflector extending along a first longitudinal axis and having an axial aperture formed therein which extends along the longitudinal axis, a first elongate light source extending along a second longitudinal axis, generally parallel to the first longitudinal axis and being arranged to illuminate the cylindrical reflector, such that light from the first elongate light source is directed onto a plane generally along a third longitudinal axis, generally parallel to the first and second longitudinal axes, a second elongate light source extending along a fourth longitudinal axis, generally parallel to the first, second and third longitudinal axes, the second elongate light source being arranged with respect to the axial aperture of the cylindrical reflector such that light from the second elongate light source is directed through the axial aperture onto the plane generally along the third longitudinal axis, and an optical element disposed along a light path between the second elongate light source and the plane and being operative to pass light from the second elongate light source to the plane and to reflect light from the plane to an optical sensor.

Further in accordance with a preferred embodiment of the present invention the first elongate light source comprises an elongate light generating element and an elongate reflector extending along a fifth longitudinal axis, generally parallel to the first, second, third and fourth longitudinal axes and being operative to reflect light from the elongate light generating element onto the cylindrical reflector.

There is also provided in accordance with yet another preferred embodiment in accordance with a preferred embodiment of the present invention an illumination system including at least two elongate light sources extending along at least two light source longitudinal light source axes, each of the at least two elongate light sources being arranged to illuminate a plane generally along a longitudinal illumination axis, generally parallel to the at least two light source longitudinal axes, and an optical element disposed along a light path between at least one of the at least two elongate light sources and having astigmatism, the optical element being operative to cause light from the at least one of the at least two elongate light sources to be smeared along the longitudinal illumination axis.

There is also provided in accordance with another preferred embodiment of the present invention an illumination system including a light source arranged to illuminate an object, a plurality of lenses imaging light from the light source reflected by the object onto a plurality of light receivers, the physical sizes of the plurality of lenses and the spacing of the plurality of light receivers being such that the plurality of lenses cannot all lie in a single plane, folding optics arranged along light paths between the plurality of lenses and the plurality of light receivers and being arranged such that notwithstanding different physical separations between ones of the plurality of lenses and corresponding ones of the plurality of light receives the light paths between the ones of the plurality of lenses and the corresponding ones of the plurality of light receivers are substantially identical.

Further in accordance with a preferred embodiment of the present invention the plurality of lenses have substantially identical focal lengths.

Additionally or alternatively the plurality of lenses image at least partially overlapping regions on the object.

There is further provided in accordance with a preferred embodiment of the present invention an inspection device including first and second light sources arranged to illuminate a substrate having reflective features thereon, the first and second light sources providing light outputs having wavelength spectra which are at mutually distinguishable, and at least one light receiver receiving light from the first light source reflected from the substrate and receiving light from the second light source transmitted via the substrate.

There is further provided in accordance with a preferred embodiment of the present invention imaging apparatus including an illuminator illuminating a region on the surface of an article. A plurality of sensors is associated with a plurality of quasi-telecentric lenses, and the sensors and lenses are arranged to simultaneously image mutually overlapping portions of the illuminated region. Preferably, principal rays imaging each part of the portion deviate less than ±10° from the normal, and more preferably they deviate less than or equal to 3.5° from the normal.

BRIEF DESCRIPTION OF THE DRAWINGS

The present invention will be understood and appreciated more fully from the following detailed description, taken in conjunction with the drawings, in which.

DETAILED DESCRIPTION OF THE PREFERRED EMBODIMENTS

Figure 1:
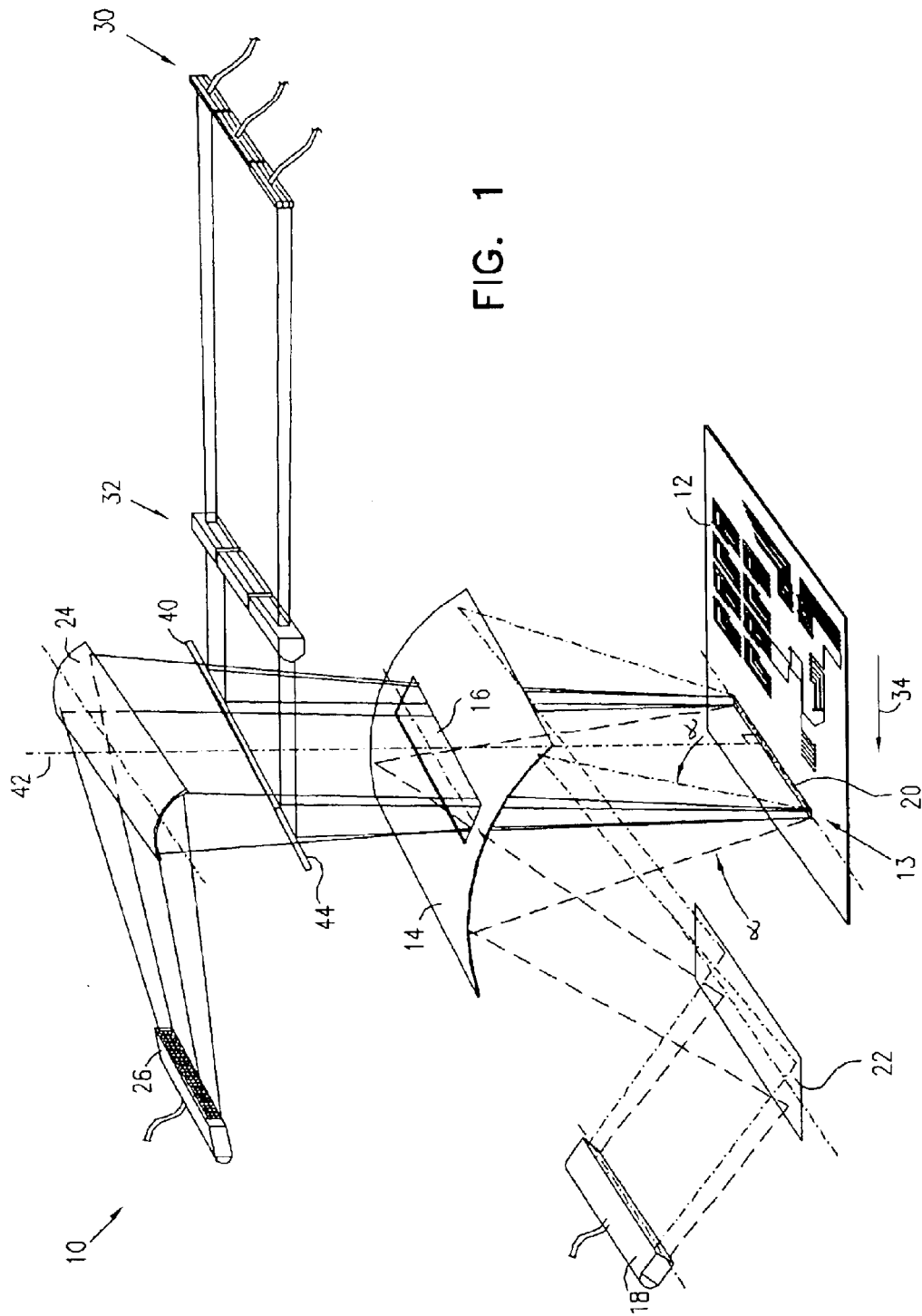
FIG. 1 is a simplified schematic illustration of an illumination and imaging system constructed and operative in accordance with a preferred embodiment of the present invention.
Figure 2:
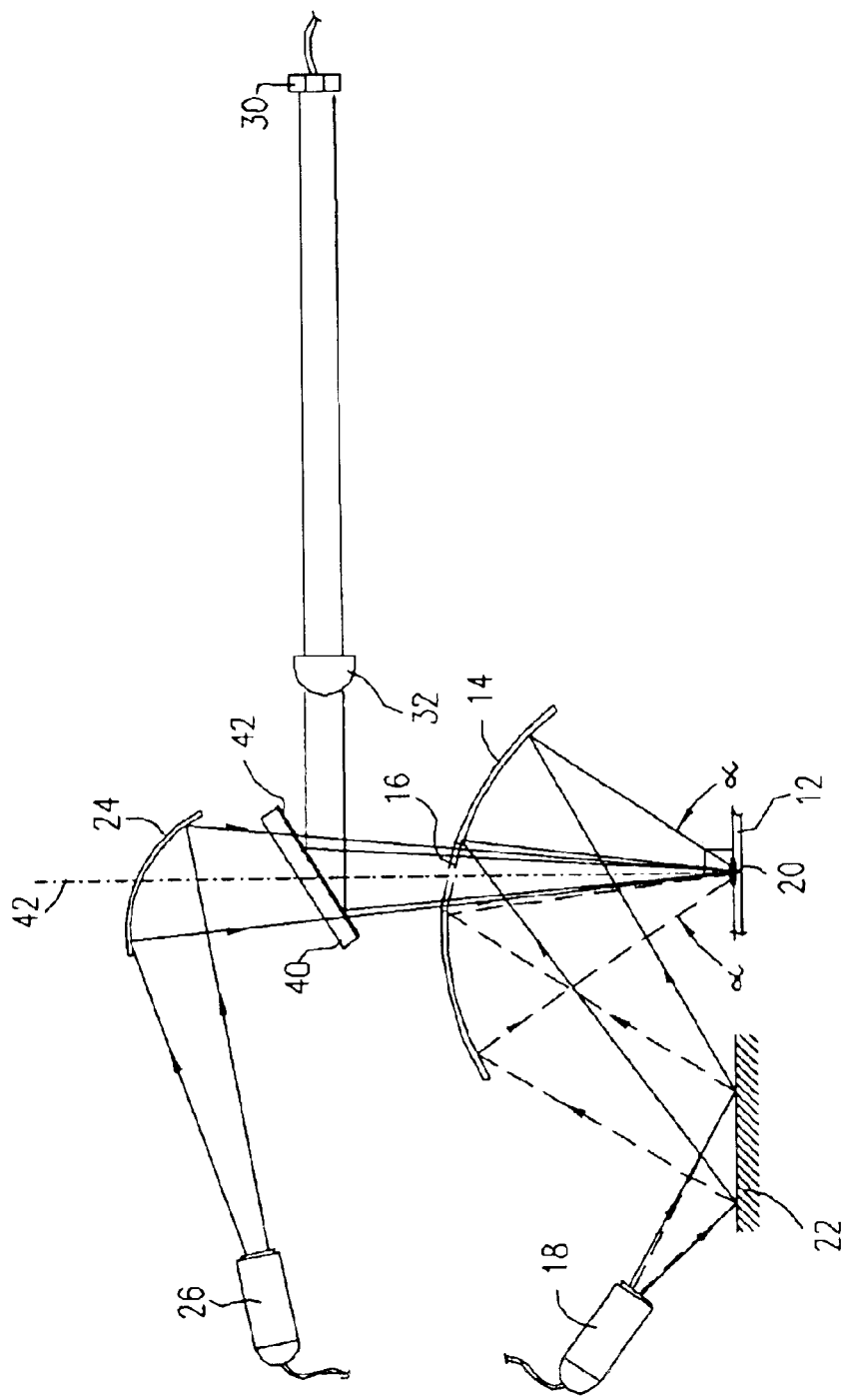
FIG. 2 is a simplified side view of the illumination and imaging system shown in FIG. 1.

Reference is now made to FIG. 1 which is a simplified schematic illustration of an illumination and imaging system 10 constructed and operative in accordance with a preferred embodiment of the present invention, and to FIG. 2 which is a simplified side view of the system of FIG. 1. Illumination and imaging system 10 typically forms part of an automated optical inspection system which comprises a first image processing subsystem running in hardware, preferably as described in copending Israel Patent Application 131092, and a second image processing subsystem running in software as described in copending Israel Patent Application filed concurrently herewith.

The illumination and imaging system of FIG. 1 can be used for the inspection of patterns on flat surfaces of articles such as electrical circuits. Such electrical circuits, include for example, printed circuit boards, ball grid array substrates, multi-chip modules and semiconductors. Other examples of articles that can be inspected using the system of FIG. 1 include reticles, lead frames and finely engraved and etched metal substrates, as may be found, for example, on medical implants. Reference herein to a patterned article is deemed to include any suitable patterned article.

Illumination and imaging system 10 is preferably operative to illuminate a portion of a surface 12 of a patterned article which is being inspected. A first reflector 14, preferably formed from a section of a cylinder having a substantially elliptical cross-section, is oriented with respect to surface 12 so as to subtend an angle α, preferably, approximately ±24° with respect to a location 13 thereon, location 13 being at or near a first focus of first reflector 14. Reflector 14 includes a centrally disposed light transmissive region, preferably an aperture 16, overlying location 13.

A first illuminator 18 is situated at or near a second focus of first reflector 14, and is configured and arranged to direct illumination onto first reflector 14 and therefrom onto surface 12 at location 13 to define a linear illuminated portion 20 of surface 12. First illuminator 18 preferably includes a bundle of 80 micron optical fibers available from Schott Corporation of Germany which are fanned out to form a fiber optic emitter preferably having dimensions of 1 mm by 100 mm. First illuminator 18 is preferably fed by a halogen projection lamp.

Preferably a planar folding mirror 22, operative to fold illumination emitted by first illuminator 18, is disposed between reflector 16 and first illuminator 18 as shown in FIG. 1.

A second reflector 24, preferably formed from a section of a cylinder having a substantially elliptical cross-section, is disposed and arranged to overlie aperture 16 so that a first focus of reflector 24 lies at or near linear illuminated portion 20.

A second illuminator 26, the intensity of which preferably is adjustable independently of the intensity of first illuminator 18, is provided at a second focus of reflector 24, and is arranged to direct illumination onto second reflector 24 and from second reflector 24 through aperture 16 onto linear illuminated region 20. Second reflector 24 and second illuminator 26 preferably are configured and arranged so that illumination from second illuminator 26 slightly overfills aperture 16. As a result, a solid angle of illumination, part of which is provided by illuminator 18 and part of which is provided by illuminator 26, fills the entire extent of angle a.

At least one, and preferably three, imaging sensors 30, are arranged to image linear illuminated region 20 via aperture 16. Quasi-telecentric imaging optics 32, described hereinbelow in greater detail with reference to FIG. 4–FIG. 6, preferably are provided. Sensors 30 may be CCD or TDI sensors, and are preferably KLI 2103 Red, Green and Blue sensor units, available from Eastman Kodak. These sensors are preferably operative to acquire polychromatic images and output reflective intensities for Red, Green and Blue spectra in the linear illuminated region 20. Preferably, patterned surface 12 is positioned on a stage (not shown) which is transported below reflector 14 in a scan direction 34, while sensors 30 image the linear illuminated region 20.

An optical element 40, preferably a highly optically flat light transmissive plane parallel plate, preferably approximately equal in length to second reflector 24, is disposed between aperture 16 and second reflector 24, defines an optical path, part of which extends along an axis 42 normal to surface 12, along which sensors 30 image linear illuminated region 20. Preferably, optical element 40 is arranged at a 45° angle relative to the plane of surface 12, and is provided with a partially silvered surface 44 on the underside thereof. Optical element 40 preferably transmits light received from second illuminator 26 via reflector 24 onto linear illuminated region 20 and directs light that is reflected from linear illuminated region 20 to sensors 30.

It is readily appreciated from the preceding discussion that the present invention provides a solid angle of intense illumination to a linear region of a workpiece using only two separately adjustable sources of illumination. First illuminator 18 and second illuminator 26 each provide illumination that is oriented along axis 42. The solid angle of the illumination provided by illuminator 26 is narrower than that of the illumination provided by illuminator 18.

It is a particular feature of the present invention that optical element 40 serves two disparate functions. Principally, it reflects light received from linear illuminated region 20 onto sensors 30 substantially without astigmatism. Secondarily it introduces astigmatism into light transmitted therethrough from reflector 24 onto linear illuminated region 20. This astigmatism is perpendicular to the longitudinal axis of linear illuminated region 20 and produces desired smearing of the illumination from reflector 24. The extent of the desired smearing is controlled by suitable orientation and the thickness of the optical element 40 relative to reflector 24 and surface 12.

Figure 3:
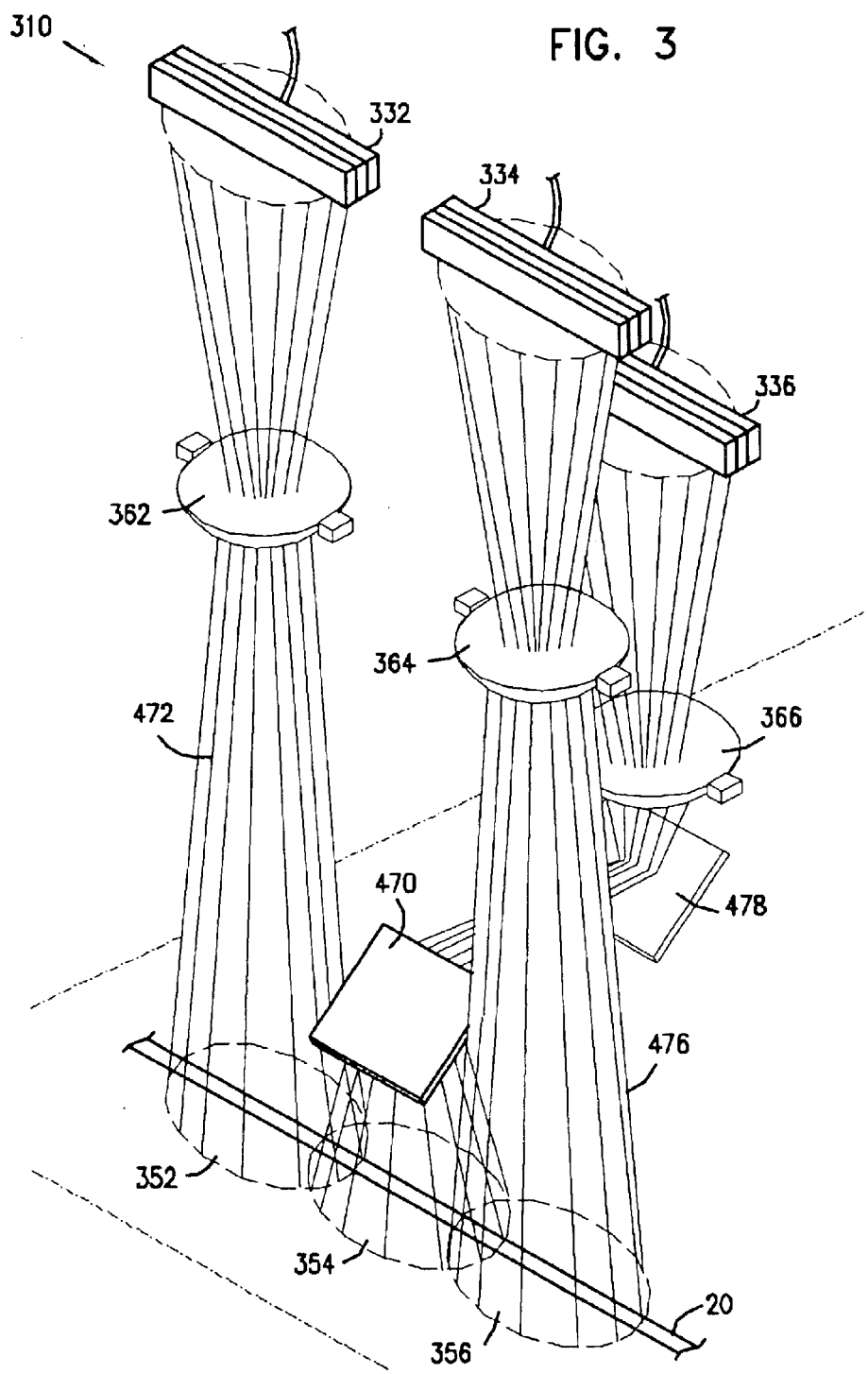
FIG. 3 is a simplified schematic illustration of a quasi-telecentric imaging system for simultaneously imaging mutually overlapping regions using multiple lenses in accordance with a preferred embodiment of the present invention.

Reference is now made to FIG. 3, which is a simplified schematic illustration of a quasi-telecentric imaging system for simultaneously imaging mutually overlapping regions using multiple lenses in accordance with a preferred embodiment of the present invention.

In systems for automated optical inspection of surfaces having a non-even surface topography, as is generally present in printed circuit boards, ball grid array substrates, lead frames, reticles, and other etched and engraved surfaces, it is generally desirable to employ an imaging system which has a high degree of telecentricity. A telecentric imaging system is an optical system having an entrance pupil located at infinity. In telecentric imaging systems, the principal ray emanating from each point on a surface being imaged is substantially parallel to the optical axis of the optical system. Consequently, all of the points on the surface are viewed at the same perspective. In order to achieve a high degree of telecentricity, the front element of a lens in the optical system is typically at least as large as its field of view.

In conventional imaging systems a high degree of telecentricity is typically obtained either by employing very large and expensive lenses to image an entire region, or by employing a plurality of smaller and less expensive lenses wherein each individual smaller lens images a relatively small region and the plurality of lenses together image the entire region.

Because of the physical size requirements of telecentric lenses as described hereinabove, in conventional multiple telecentric lens configurations, the individual lenses are spaced apart from each other and image non-mutually overlapping regions. Thus, in conventional telecentric imaging systems, in order to image an entire surface, it is necessary either to scan the surface in multiple passes or to stagger multiple rows of telecentric lenses.

As seen in FIG. 3, a quasi-telecentric imaging system 310 is provided for simultaneously imaging mutually overlapping regions using multiple lenses which are configured and arranged in accordance with a preferred embodiment of the present invention.

Quasi-telecentric imaging system 310, includes at least two, and preferably three or more, RGB sensor units 332, 334 and 336, which together make up sensor 30 (FIG. 1). In the preferred arrangement shown, each of the three sensors 332, 334 and 336 is operative to simultaneously view a corresponding one of a mutually overlapping viewing region 352, 354, and 356 along surface 12 (FIG. 1), via respective lenses 362, 364 and 366 associated therewith. Preferably lenses 362, 364 and 366 are Macrosimar 120 mm, F5.6 lenses.

Sensors 332, 334 and 336 and lenses 362, 364 and 366 are preferably arranged so that overlapping viewing regions 352, 354 and 356 intersect linear illuminated region 20 (FIG. 1). It is readily appreciated that only those parts of viewing regions 352, 354 and 356 which fall along linear illuminated region 20 are imaged by sensors 332, 334 and 336.

Figure 4:
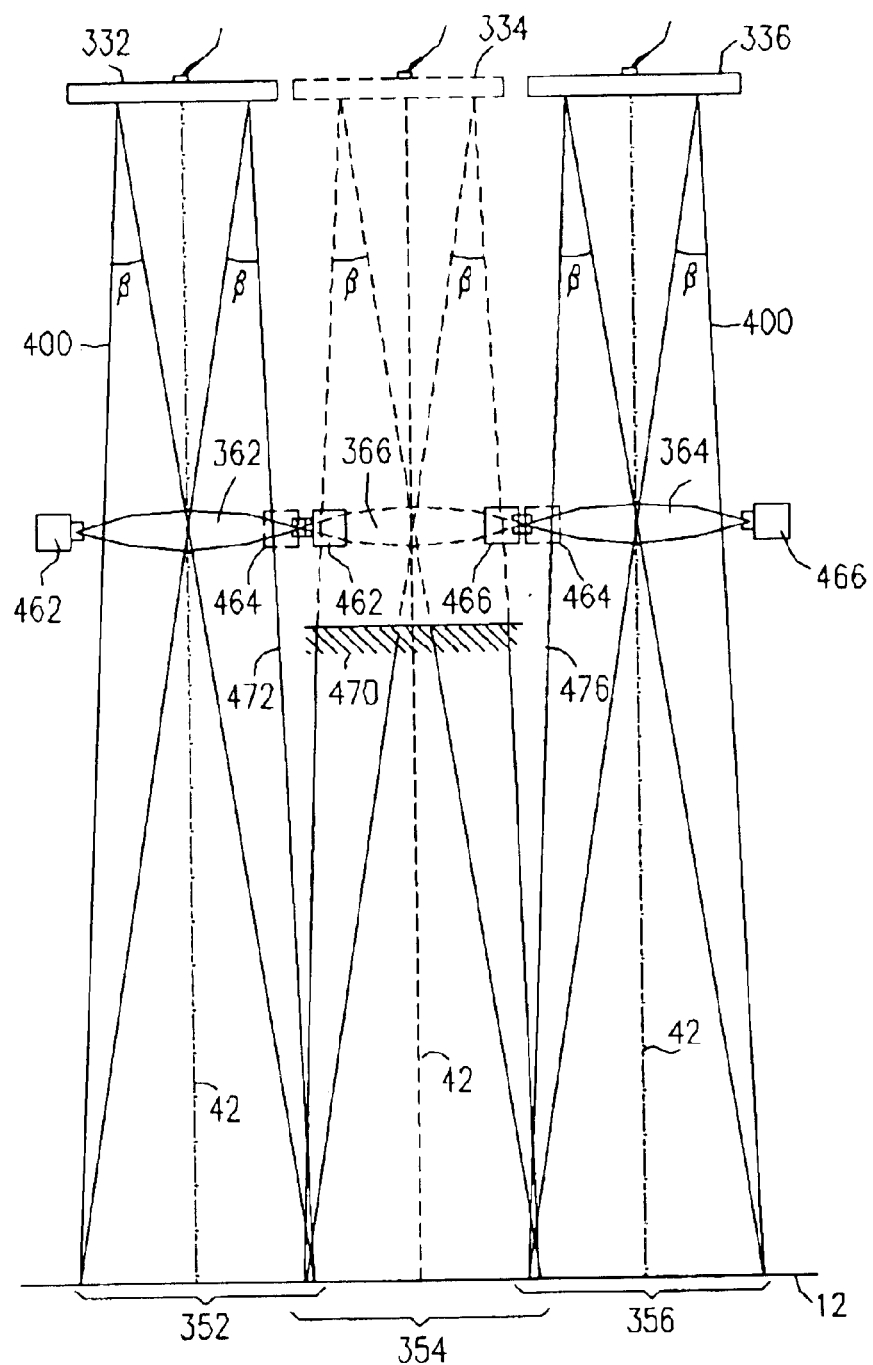
FIG. 4 is a simplified ray diagram of the quasi telecentric imaging system shown in FIG. 3.

In order to explain the structure of FIG. 3, reference is made additionally to FIG. 4, which is a simplified optical diagram of quasi telecentric imaging system 310. Rays 400 are shown in the diagram as subtending an angle β which is exaggerated for the sake of simplicity and clarity of illustration. In a quasi telecentric imaging system such as that of the present invention, the maximum deviation from the optical axis 42 (FIG. 1), normal to surface 12 (FIG. 1) of the principal rays reaching sensors 332, 334 and 336 from portions of respective viewing regions 352, 354 and 356 is less than ±5°, and more preferably less than or equal to ±3.7°.

Each of telecentric lenses 362, 364 and 366 is preferably held by a respective mounting, designated by respective reference numerals 462, 464 and 466, and is located an equal optical distance from surface 12 and sensors 432, 434 and 436. Together with their respective mountings, lenses 362, 364 and 366 are typically larger than respective viewing regions 352, 354 and 356.

In order to provide simultaneous viewing of mutually overlapping viewing regions 352, 354 and 356 and to accommodate lenses 362, 364 and 366 a first planar folding mirror 470 is preferably interposed between telecentric lens 366 and viewing region 354. A second planar folding mirror 478, interposed between first planar folding mirror 470 and telecentric lens, is optionally provided. Planar folding mirror 470 is preferably sufficiently large to provide an unhindered view of viewing region 354, and is arranged to be situated intermediate rays 472 and 476 entering respective lenses 362 and 364 so as not to interfere with their view of mutually overlapping viewing regions 352 and 356. It is noted that first planar folding mirror 470 folds the rays that are shown in FIG. 4 as extending between overlapping portion 354 and sensor unit 334. Thus it is appreciated that sensor unit 334 and telecentric lens 366 and mountings 464 lie in a different plane than sensor units 332 and 336, telecentric lenses 362 and 364, and mountings 462 and 466 respectively.

Figure 5:
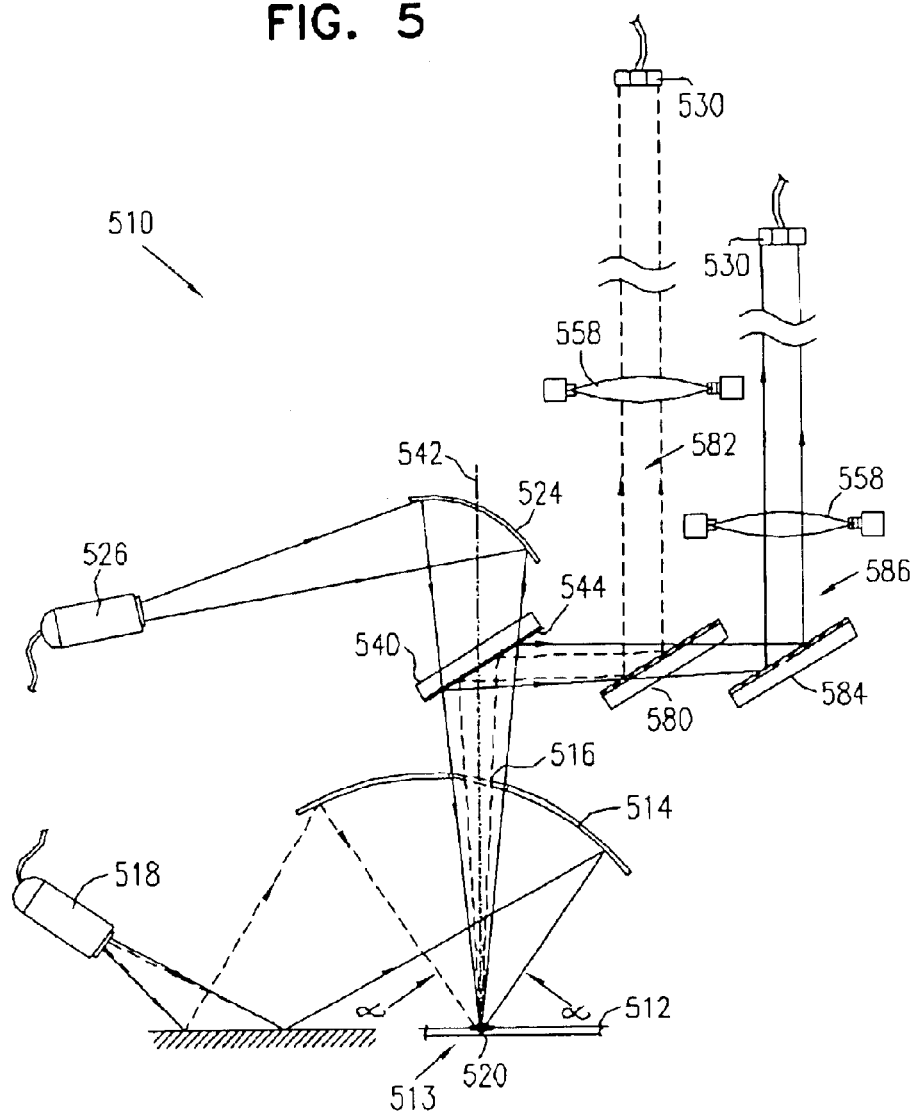
FIG. 5 is a simplified side view of a preferred embodiment of a quasi-telecentric imaging system of the type shown in FIG. 3 and FIG. 1.

Reference is made to FIG. 5 which is a simplified side view illustration of an illumination and imaging system 510 for illuminating and imaging a linear illuminated region on a flat patterned article 512. The embodiment of FIG. 5 is an alternative to that of FIGS. 1–4 and is believed to be the preferred embodiment. The illumination and imaging system 510 preferably employs quasi-telecentric imaging combined with an illumination system which is identical to that described hereinabove with reference to FIG. 1 and FIG. 2.

Illumination and imaging system 510 preferably includes a first reflector 514, preferably formed from a section of a cylinder having a substantially elliptical cross-section, which is oriented with respect to a surface 512 of an article so as to subtend and angle α, preferably ±24°, with respect to a location thereon 513, which is arranged to be at or near a first focus of reflector 514. First reflector 514 preferably includes a centrally disposed light transmissive region, preferably an aperture 516, overlying location 513.

A first illuminator 518 is situated at or near a second focus of first reflector 514 and is configured and arranged to direct illumination onto first reflector 514 and therefrom onto surface 512 at location 513 to define a linear illuminated portion 520 of surface 512. First illuminator 518 is preferably configured and arranged similarly to illuminator 18 as described hereinabove with reference to FIG. 1. Preferably a planar folding mirror 522, operative to fold illumination emitted by first illuminator 518, is disposed between reflector 514 and first illuminator 518.

A second reflector 524, preferably formed of a section of a cylinder having a substantially elliptical cross-section, is disposed and arranged to overlie aperture 516 so that a first focus of reflector 524 lies at or near linear illuminated portion 520.

A second illuminator 526, the intensity of which preferably is adjustable independently of the intensity of first illuminator 518, is provided at a second focus of reflector 524, and is arranged to direct illumination onto second reflector 524 and from second reflector 524 through aperture 516 onto linear illuminated region 520. Second reflector 524 and second illuminator 526 preferably are configured and arranged so that illumination from second illuminator 526 slightly overfills aperture 516.

Preferably three imaging sensors 530 (of which only two are seen), are arranged to image linear illuminated region 520 via aperture 516. Sensors 530 may be CCD or TDI sensors, and are preferably KLI 2103 Red, Green and Blue sensor units, available from Eastman Kodak. These sensors are preferably operative to acquire polychromatic images and to output reflective intensities for Red, Green and Blue spectra in the linear illuminated region 20.

An optical element 540, preferably a highly optically flat light transmissive plane parallel plate, is disposed between aperture 516 and second reflector 524, defines an optical path, part of which extends along an axis 542, normal to surface 512, along which sensors 530 image linear illuminated region 520. Preferably, optical element 540 is arranged at a 45° angle relative to the plane of surface 512, and is provided with a partially silvered surface 544 on the underside thereof. Optical element 540 preferably transmits light from second illuminator 526 via reflector 524 to linear illuminated region 520 and directs light that is reflected from linear illuminated region 520 to sensors 530.

Each sensor 530 is preferably associated with a quasi-telecentric imaging lens 558. Each sensor 530 is operative to simultaneously image a mutually overlapping portion of linear illuminated region 520.

A first planar folding mirror 580 is disposed along a first optical path 582, shown in broken lines, extending from linear illuminated region 520 to a first sensor 530 via a first lens 558. A second planar folding mirror 584 is disposed in a second optical path 586, shown in solid lines, extending between linear illuminated region 520 and a second sensor 530 via a second lens 558. A third planar folding mirror (not seen in FIG. 5) is disposed in a third optical path (not seen in FIG. 5) which is hidden by optical path 586, extending between linear illuminated region 520 and a third sensor 530 via a third lens 558, both of which are not seen in FIG. 5.

It is noted that first planar folding mirror 580 is preferably sufficiently large to provide an unhindered view of a second portion of linear illuminated region 520 and is arranged to be situated intermediate optical paths entering respective first and third lenses 558 so as not to interfere with their view of mutually overlapping portions of linear illuminated region 520.

It is additionally noted that despite the different locations of the first, second and third mirrors, the respective optical paths through the first, second and third lenses 558 are each situated at an equal optical distance from the respective sensor 530, and each lens 558 is situated at an equal optical distance from linear illuminated region 520.

Figure 6:
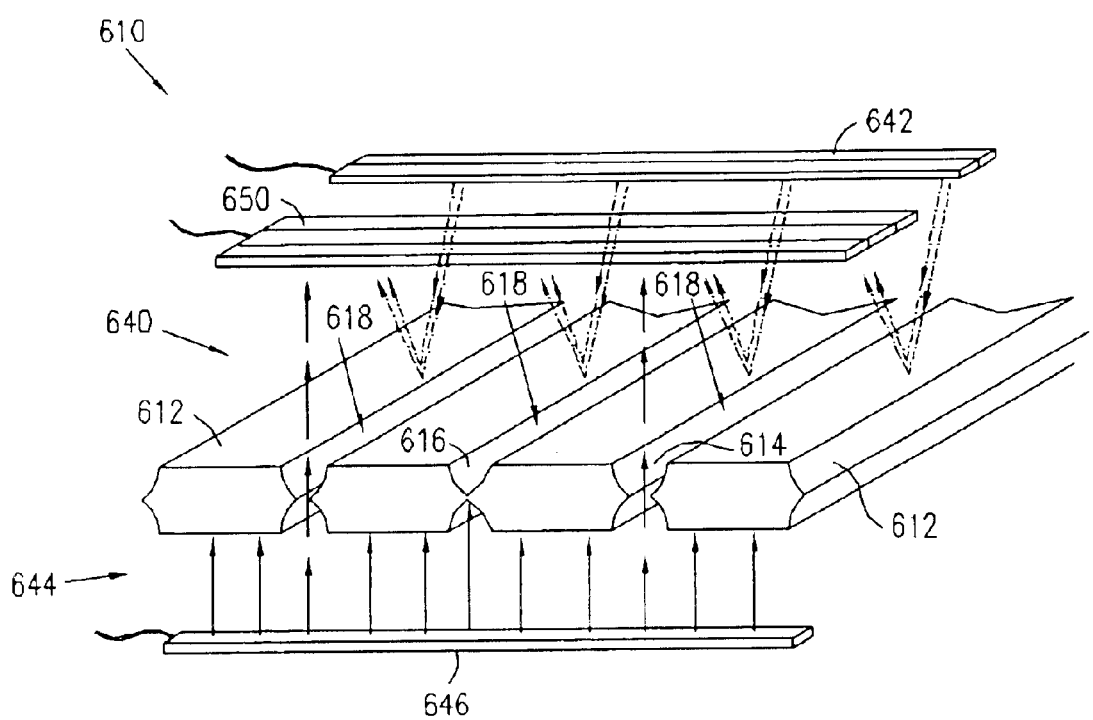
FIG. 6 is a simplified pictorial illustration of an imaging system for imaging a patterned object having voids, using illumination in distinguishable spectral ranges in accordance with a preferred embodiment of the present invention.

Reference is now made to FIG. 6, which is a simplified pictorial illustration of an imaging system 610 for imaging a patterned object having apertures, using illumination in mutually distinguishable spectral ranges in accordance with a preferred embodiment of the present invention. The imaging system 610 is described herein with reference to the inspection of lead frames, for which its is particularly suited. It is readily appreciated that the imaging system 610 is not limited to use in inspecting lead frames and is generally useful for optically inspecting any suitable patterned surface that is characterized by apertures, voids and through holes.

Lead frames typically comprise a plurality of leads 612, which have a width and height dimension and which are typically formed via a suitable pressing, engraving or etching process, and which are typically coated with a metal coating. A typical lead frame is formed of copper, and coated at various locations thereon with silver and gold. Leads 612 are generally optically inspected to determine that each of the leads is separated one from another by a separation 614, and that no pair of adjacent leads is connected by a bridge 616.

It is readily appreciated due to the depth dimension of leads 612, and due to the existence of non-vertical edges between adjacent leads, which are generally the result of pressing, engraving and etching processes used to manufacture lead frames, the intensity of reflected light in regions 618 between leads 612 is typically considerably less than the intensity of light reflected from the horizontal regions of the leads. Accordingly, the intensity of light reflected from a bridge 616 may be very close to zero as is characteristic of regions having a separation 614 between adjacent leads.

In a preferred embodiment of the present invention, an illuminator is preferably provided to illuminate a first side 640 of leads 612 in or more spectral ranges which facilitate the detection of combinations of materials commonly present on lead frames. For example, a first illuminator 642 is preferably configured to provide substantially red and green illumination, which together generally facilitate the identification of regions of copper, gold and silver.

A second illuminator, preferably emitting in a spectral range which is distinguishable from the spectral range of first illuminator 642, is provided to illuminate a second side 644 of leads 612. For example, a second illuminator 646 is configured to provide substantially blue illumination, or illumination in a non-visible spectrum, to second side 644.

A sensor 650 is preferably provided to view a portion of first side 640, and is operative to separately sense the intensity of light in each of the spectral ranges emitted by first illuminator 642 and by second illuminator 646. Thus, sensor 650 is operative to sense the intensity of light provided by first illuminator 642 and reflected by the first side 640, and to separately sense light provided by second illuminator 646 and transmitted via apertures located in and between leads 612, for example light transmitted through separations 614.

It is readily appreciated that because the spectrum of reflection of light provided by first illuminator 642 is distinguishable from the spectrum of light provided by second illuminator 646, it is possible to simultaneously provide an output indicating the existence of voids and apertures in and between leads 612, and to inspect leads for defects which are detectable by analyzing reflected light, for example, defects in coatings on leads 612.

It is appreciated that various features of the invention which are, for clarity, described in the context of separate embodiments may also be provided in combination in a single embodiment. Conversely, various features of the invention that are, for brevity, described in the context of a single embodiment may also be provided separately or in any suitable combination. The scope of the present invention is not limited to what has been described hereinabove but rather also includes modifications and variations thereof as would occur to persons skilled in the art upon reading the foregoing description and which are not in the prior art.

What is claimed is:

1. An illumination system comprising:
   at least one reflector subtending an angle with respect to a location on a surface of an article and having formed therein a light transmissive region;
   a light source consisting of first and second light illuminators, said light transmissive region being configured to permit light from a first one of said first and second illuminators to pass therethrough; and
   an optical element including at least one reflecting surface disposed intermediate said first one of said first and second illuminators and said light transmissive region for directing the light output of said first one of said first and second illuminators through said light transmissive region;
   said first and second illuminators each providing a light output, the light outputs from both of said first and second illuminators being directed to impinge on said location on said surface of an article from within said angle, at least one of said light outputs being reflected by said reflector, wherein a light output from said first illuminator illuminates said location from within a solid angle of illumination that is narrower than said angle.

2. An illumination system according to claim 1, wherein said light transmissive region is an aperture formed in said reflector.

3. An illumination system according to claim 1, further comprising an optical assembly disposed along an optical path extending between said optical element and said location on the surface of an article for directing light reflected from said location on the surface of an article to a light sensor.

4. An illumination system according to claim 3, wherein said optical assembly is generally transmissive to said the light output of said first one of said first and second illuminators directed through said light transmissive region onto said location on the surface of an article and generally reflective of light reflected from said location on the surface of an article.

5. An illumination system according to claim 1, further comprising a reflective surface disposed intermediate a second one of said first and second illuminators and said reflector for directing the light output of said second one of said first and second light sources onto said reflector.

6. An illumination system according to claim 1, wherein said at least one reflector is an elliptical reflector and a second one of said first and second illuminators and said location on the surface of an article are each located at a locus of said elliptical reflector.

7. An illumination system according to claim 6, wherein said at least one reflector comprises two spaced apart reflectors which together define a section of an ellipse.

8. An illumination system according to claim 1, wherein said first and second illuminators comprise independently controllable illuminators.

9. An illumination system according to claim 1, wherein said first and second illuminators comprise a plurality of light emitters.

10. An illumination system according to claim 9, wherein said plurality of light emitters comprises a plurality of optical fibers receiving light from a projection lamp.

11. An illumination system comprising:
- a cylindrical reflector extending along a first longitudinal axis and having an axial aperture formed therein which extends along said longitudinal axis;
- a first elongate light source extending along a second longitudinal axis, generally parallel to said first longitudinal axis and being arranged to illuminate portions of said cylindrical reflector disposed along both sides of said axial aperture, such that light from said first elongate light source is directed by said portions onto a plane generally along a third longitudinal axis, generally parallel to said first and second longitudinal axes;
- a second elongate light source extending along a fourth longitudinal axis, generally parallel to said first, second and third longitudinal axes, said second elongate light source being arranged with respect to said axial aperture of said cylindrical reflector such that light from said second elongate light source is directed through said axial aperture onto said plane generally along said third longitudinal axis; and
- an optical element disposed along a light path between said second elongate light source and said plane and being operative to pass light from said second elongate light source to said plane and to reflect light from said plane to an optical sensor.

12. An illumination system comprising: a cylindrical reflector extending along a first longitudinal axis and having an axial aperture formed therein which extends along said longitudinal axis;
- a first elongate light source extending along a second longitudinal axis, generally parallel to said first longitudinal axis and being arranged to illuminate said cylindrical reflector, such that light from said first elongate light source is directed onto a plane generally along a third longitudinal axis, generally parallel to said first and second longitudinal axes;
- a second elongate light source extending along a fourth longitudinal axis, generally parallel to said first, second and third longitudinal axes, said second elongate light source being arranged with respect to said axial aperture of said cylindrical reflector such that light from said second elongate light source is directed through said axial aperture onto said plane generally along said third longitudinal axis; and
- an optical element disposed along a light path between said second elongate light source and said plane and being operative to pass light from said second elongate light source to said plane and to reflect light from said plane to an optical sensor;
- wherein said first elongate light source comprises an elongate light generating element and an elongate reflector extending along a fifth longitudinal axis, generally parallel to said first, second, third and fourth longitudinal axes and being operative to reflect light from said elongate light generating element onto said cylindrical reflector.

* * * * *